United States Patent
Ezekwe et al.

(10) Patent No.: US 7,118,771 B2
(45) Date of Patent: Oct. 10, 2006

(54) FOOD COMPOSITIONS COMPRISING WATERLEAF LEAVES AND METHODS OF USING THEREOF

(75) Inventors: Michael Obi Ezekwe, Vicksburg, MS (US); Samuel Ayuk Besong, Dover, DE (US); Patrick Emeka Igbokwe, Vicksburg, MS (US); Edith Ifeyinwa Ezekwe, Vickburg, MS (US)

(73) Assignee: Alcorn State University, Alcorn State, MS (US)

( * ) Notice: Subject to any disclaimer, the term of this patent is extended or adjusted under 35 U.S.C. 154(b) by 0 days.

(21) Appl. No.: 10/791,310

(22) Filed: Mar. 1, 2004

(65) Prior Publication Data

US 2004/0234635 A1    Nov. 25, 2004

Related U.S. Application Data

(60) Provisional application No. 60/451,536, filed on Mar. 3, 2003.

(51) Int. Cl.
*A61K 36/00* (2006.01)
(52) U.S. Cl. ...................... 424/774; 424/725
(58) Field of Classification Search ................ 424/774, 424/725
See application file for complete search history.

(56) References Cited

U.S. PATENT DOCUMENTS 5,688,508 A    11/1997    Ezekwe et al.

OTHER PUBLICATIONS

Ezekwe et al., "Beneficial Influence of Purslane and Waterleaf Supplementation on Cardiovascular Disease Risk in Humans," FASEB Journal, Mar. 20, 2002, vol. 16, No. 4, pp. A639.*

Internet website http://www.news.wisc.edu/3358.html. 4 pages. Jun. 17, 1998.*

Adams, C.D. Flowering Plants of Jamaica. University of West Indies. 1972. p. 268.

Akachuku, C.O. and M.A.O. Fawusi. Growth Characteristics, Yield and Nutritive Value of Waterleaf, *Talinum triangulare* (Jacq.) Willd in a Semi-wild Environment, Discovery and Innovation. Jun. 1995. vol. 7, pp. 163-172.

Cave, Jr., W.T. Dietary n-3 (w-3) polyunsaturated fatty acid effects on animal tumorigenesis. The FASEB Journal. May 1991. vol. 5, pp. 2160-2166.

Chan, J.K., B.E. McDonald, J.M. Gerrard, V.M. Bruce, B.J. Weaver, and B.J. Holub. Effect of Dietary Alpha-Linolenic Acid and Its Ratio to Linoleic Acid on Platelet and Plasma Fatty Acids and Thrombogenesis. LIPIDS. 1993. vol. 28, pp. 811-816.

Egwin, P.O. Composite Quality Cost Index (CQCI): A New Biochemical-Economic Rating System for Vegetable Food Proteins. Nigerian Journal of Science. 1979. vol. 13, pp. 323-332.

Mabberley, D.J. The plant-book. A portable dictionary of the higher plants. Cambridge University Press. 1990. p. 568.

Sridhar, R. and G. Lakshminarayana. Lipid Classes, Fatty Acids, and Tocopherols of Leaves of Six Edible Plant Species. J. Agric. Food Chem. 1993. vol. 41, pp. 61-63.

* cited by examiner

*Primary Examiner*—Christopher R. Tate
*Assistant Examiner*—S. B. McCormick-Ewoldt
(74) *Attorney, Agent, or Firm*—Lawrence Arthur Schemmel

(57) ABSTRACT

This invention relates to and is drawn to food compositions including waterleaf leaves harvested at full bloom. The present invention further relates to and is drawn to methods of reducing the risks of cardiovascular diseases by reducing total plasma cholesterol and plasma LDL-cholesterol and increasing plasma HDL-cholesterol and blood hematocrit using the present food compositions of waterleaf leaves, in addition to methods of preventing and treating coronary heart disease using the present food compositions.

15 Claims, 5 Drawing Sheets

FOOD COMPOSITIONS COMPRISING WATERLEAF LEAVES AND METHODS OF USING THEREOF

CROSS-REFERENCE TO RELATED APPLICATION

This application is a regular National application claiming priority from Provisional Application, U.S. Application Ser. No. 60/451,536 filed Mar. 3, 2003. The entirety of that provisional application is incorporated herein by reference.

FIELD OF THE INVENTION

The invention relates to novel food compositions including waterleaf leaves harvested at full bloom. The present invention is further drawn to methods of reducing the risks of cardiovascular diseases in humans and improving meat quality in animals with the present food compositions of waterleaf leaves, in addition to methods of preventing and treating coronary heart disease with the food compositions.

BACKGROUND OF THE INVENTION

An ever-increasing concern exists today regarding high blood lipid levels experienced by over sixty million Americans, especially levels of cholesterol and triglycerides. A large body of evidence also indicates that improving dietary habits can reduce the risk or delay the onset of chronic diseases such as heart disease and stroke. Growing consumer demand for non-traditional foods and interest in self-medication are supporting markets for special food products at the same time that health care costs continue to exceed one trillion dollars annually. A priority for newly-designed foods must be to restore Omega-3 fatty acids (n-3) to human diets and also to balance the ratio of Omega-6 (n-6) fatty acids to n-3 fatty acids in human diets. Low-fat diets currently recommended for reducing total cholesterol and low-density lipoproteins ("LDL-cholesterol") also increase plasma triglycerides and decrease high-density lipoproteins ("HDL-cholesterol") concentrations, thus potentially increasing the risk of cardiovascular disease. Nutrition scientists are working to create and identify foods from plants with functional properties that have specific physiological and/or nutritional effects that improve health.

The present invention encompasses the process of reducing total plasma cholesterol and plasma LDL-cholesterol, while maintaining normal plasma triglyceride levels, and of increasing blood hematocrit and plasma HDL-cholesterol levels in humans with elevated blood lipid levels and in animals by the use of natural components of waterleaf (genus *Talinum*).

*Talinum* is a small genus of the purslane family (Portulacacae), which appears to possess a unique nutritional potential. Waterleaf is in the genus *Talinum* and the species *triangulare* and is a leafy vegetable found in West Africa, the West Indies, South America (Adams, et al., Flowering Plants of Jamaica, Pukl, University of West Indies, (1972)) and the warmer parts of the world (Mabberly, The Plant Book: A Portable Dictionary of Higher Plants, Cambridge University Press, Cambridge, Mass. (1990)). The leaves and tender stems of waterleaf are consumed as a vegetable or as the constituent of a sauce by the populations of the areas where it is grown. Waterleaf grows spontaneously during the growing season, and it is common in a variety of habitats including roadsides, open fields, and abandoned agricultural lands. Although it is extensively consumed in the diet of populations where it is abundant, not much is known about its nutritive value. Waterleaf's crude protein content compares favorably with that of cowpea, peanut, millet, and cashew nuts (Egwin, Composite Quality Cost Index (CQCI): A New Biochemical Rating System for Vegetable Food Protein, Nig. J. Sci. 13:323–329 (1979)). Akachuku and Fawusi (Growth Characteristics, Yield and Nutritional Value of Waterleaf, Talinum Triangulare (Jacq) Wild in a Semi-Wild Environment, Discovery and Innovation 7:163–172 (1995)) also reported crude protein content of waterleaf leaves and tender stems as high as 29.4% and 13.4%, respectively. Sridhar and Lakahminarayana (Lipid Classes, Fatty Acids, and Tocopherols of Leaves of Six Edible Plant Species, J. Agric. Food Chem 41:61–63 (1993)) reported high total lipids, essential oils, and alpha-tocopherols and beta-tocopherols in *Talinum triangulare*.

A paucity of information exists on the health and nutritional benefits of waterleaf in humans and/or animals. Although purslane has been shown to possess nutritional qualities for reducing serum cholesterol and serum triglycerides in laboratory animals (U.S. Pat. No. 5,688,508), the present invention shows for the first time that waterleaf contains superior nutritional qualities that, when consumed by humans, vastly improves human health. Waterleaf contains a rich source of n-3 fatty acids and other nutrients that the present invention shows reduces harmful total plasma cholesterol and plasma LDL-cholesterol and increases beneficial plasma HDL-cholesterol and blood hematocrit in hypercholesterolemic humans. Waterleaf, compared to purslane, is an easier plant to grow, grows more efficiently and abundantly, has more aggressive growth characteristics, and has no known insect pests, thereby potentially serving a larger portion of the population. Waterleaf has higher levels of nutritionally-important vitamins (such as vitamin C, vitamin E, and Beta-carotene), minerals (such as calcium, potassium, and magnesium), and soluble fiber (pectin) than does purslane, all of which contribute to waterleaf's highly-elevated antioxidant values and its total biological effect. The combination in one plant species of n-3 fatty acids, antioxidants, and pectin that consequently has a positive and beneficial influence in reducing the risk of cardiovascular diseases in humans is a unique attribute of waterleaf that has not been shown to exist until the present invention.

The present inventors have designed food compositions comprising waterleaf and methods of reducing harmful blood cholesterols and simultaneously increasing beneficial blood cholesterols and vitamin and mineral levels using such food compositions and of treating and preventing coronary heart disease using such food compositions, all of which create potential for large-scale agricultural and biomedical utilization and applicability to a large segment of the population.

SUMMARY OF THE INVENTION

One object of the present invention is drawn to food compositions comprising waterleaf leaves wherein said waterleaf leaves have been harvested from a plant at full bloom.

An additional object of the present invention is drawn to methods of reducing total plasma cholesterol and plasma LDL-cholesterol and increasing plasma HDL-cholesterol and blood hematocrit using the present food compositions.

Another object of the present invention encompasses methods of reducing total plasma cholesterol and plasma LDL-cholesterol and increasing plasma HDL-cholesterol and blood hematocrit in hypercholesterolemic humans using the present food compositions.

Another object of the present invention is drawn to methods of reducing total plasma cholesterol and plasma LDL-cholesterol and increasing plasma HDL-cholesterol and blood hematocrit in meat animals using the present food compositions.

An additional object of the present invention encompasses methods of reducing total plasma cholesterol and plasma LDL-cholesterol and increasing plasma HDL-cholesterol in meat animals using the present food compositions, thereby resulting in improved meat animal quality and in meat quality.

An additional object of the present invention encompasses methods of preventing or treating coronary heart disease using the present food compositions.

Yet another object of the present invention encompasses methods of preventing or treating coronary heart disease in humans using the present food compositions.

With the foregoing and other objects, features, and advantages of the present invention that will become apparent hereinafter, the nature of the invention may be more clearly understood by reference to the following detailed description of the preferred embodiments of the invention and to the appended claims.

DETAILED DESCRIPTION OF THE INVENTION

Figure 1:
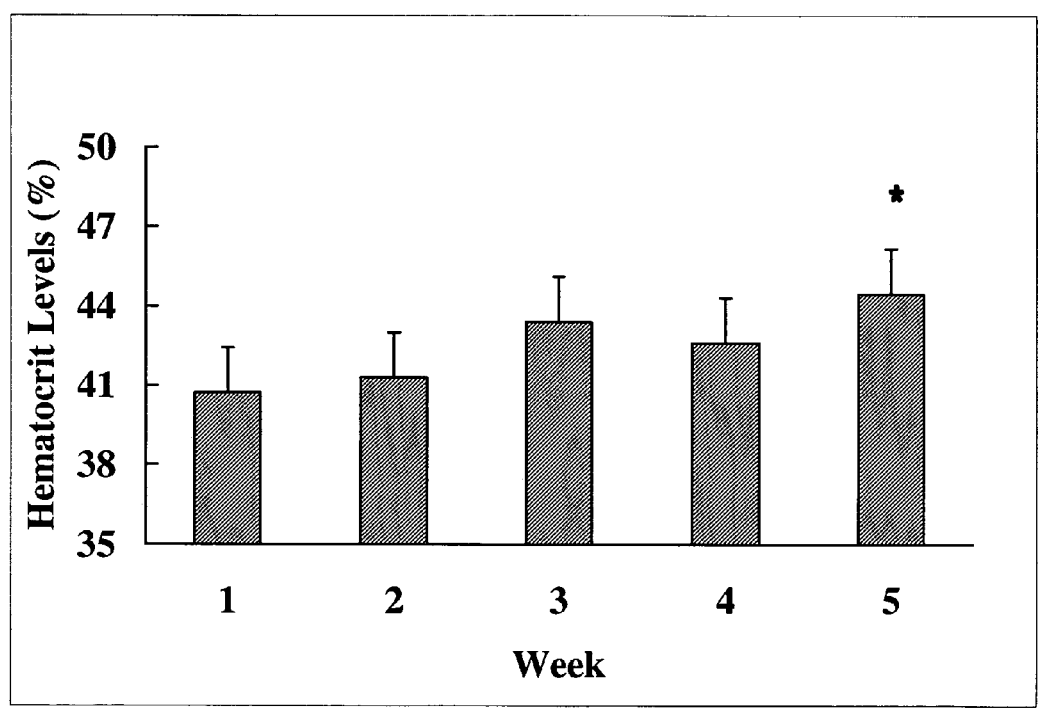
FIG. 1 is a graphical illustration of the changes in hematocrit levels in hypercholesterolemic human adults fed 6 grams per day (g/d) of freeze-dried leaf supplements of waterleaf for 5 weeks. Hematocrit levels increased at Week 5 relative to pretreatment (Week 1) levels.

Functional foods and health protectants (neutracetical and phytochemicals) are perceived as one of the opportunities in agricultural and biomedical research for improving human health in the $21^{st}$ century. The present day Western diet has shifted to unproportional consumption of n-6 fatty acids abundant in oil seeds with little or no n-3 fatty acids. High blood lipids, cholesterol, and triglycerides are major risks for cardiovascular heart disease for over sixty million Americans.

Diets rich in linolenic fatty acids (18-3n-3) have been shown to potentially reduce the formation of certain tumors and cardiovascular diseases (Chan, et al., Effect of Dietary α Linolenic Acid and Its Ratio to Linolenic Acid on Platelet and Plasma Fatty Acids and Thrombogenesis, Lipids 28:811–817 (1993); Cave, Dietary n-3 (W-3) Polyunsaturated Fatty Acids Effects on Animal Tumorigenesis FASEB J. 5:2160 (1991)). New sources of n-3 fatty acids and other essential nutrients have been identified from plants such as waterleaf with the potential to restore a balance of nutrients in human diets. Waterleaf plant contains a rich source of n-3 fatty acids and other nutrients including vitamins C and E, Beta-carotene, glutathione, crude protein and pectin.

The present invention in its preferred embodiment encompasses food compositions comprising waterleaf leaves harvested at full bloom as well as methods of reducing the risks of cardiovascular heart disease by reducing total plasma cholesterol and plasma LDL-cholesterol and by increasing plasma HDL-cholesterol and blood hematocrit using the present food compositions. The present invention further encompasses methods of preventing and treating coronary heart disease using the present food compositions.

Waterleaf seeds (*Talinum triangulare*) were planted at Alcorn State University Experiment Station in Lorman, Miss., during the Spring of 2000 and 2001. The plants were harvested at full bloom and, as the plots regenerated, harvesting was repeated. The leaves of each harvested group of plants were removed and lyophilized for 36 hours using a laboratory freeze dryer Model Labconco Lyph Lock 12. The lyophilized leaves were analyzed for proximate composition and fatty acid profile. The freeze-dried leaves were smashed into a leaf powder of 3-gram supplements, which were then packed and sealed in separate plastic bags.

Twenty-one (21) free-living human adult participants, having total plasma cholesterol concentrations of equal to or greater than 200 mg/dl, were selected after an initial screening with a cholesterol meter. Cholesterol values were confirmed by analysis of plasma samples using a Wako cholesterol kit (Wako Laboratories, Richmond, Va.). The participants were weighed and assigned to the experimental treatment. All participants were determined to be hypercholesterolemic since they each had at least 200 mg/dl concentrations of total plasma cholesterol. For this experiment, a level of 200 mg/dl or more was considered to be an above-normal or high cholesterol level. All participants were instructed to follow American Heart Association Diet 1 (20% crude protein (cp), 30% fat, and 50% carbohydrates). After 2 weeks of acclimation on American Heart Association Diet 1, the participants, serving as their own controls, consumed 3 grams of waterleaf supplement with their lunch meals and 3 grams of waterleaf supplement with their dinner meals, for a total of 6 grams per day. American Heart Association Diet 1 was followed by each participant during the 2-week acclimation period and throughout the experimental period. Three (3) grams of the freeze-dried supplements were consumed during daily supervised lunch meals. The participants were given another three (3) gram supplement pack which was consumed with their daily dinner meals at their own homes, thereby completing the 6 gram daily intake. The participants were provided with an adequate number of supplements for both lunch and dinner meals on weekends and holidays during the 5-week experimental period. Blood samples were taken from each participant before the experiment began and once each week during the experiment. Blood hematocrit, plasma glucose, total cholesterol, triglyceride, LDL-cholesterol, and HDL-cholesterol levels were recorded and analyzed using kits from Sigma, St. Louis, Mo., and Wako Laboratories, Richmond, Va.

The present invention utilized hypercholesterolemic adult human participants to demonstrate the ability of waterleaf supplements to lower blood cholesterol in humans with high blood cholesterol. This experiment shows that dietary means of cholesterol reduction work best at above-normal cholesterol levels. The dietary methods of the present invention that reduce harmful cholesterol and increase beneficial cholesterol also indicate applicability to diets for all monogastric and grazing animals. Of particular importance are the methods of the invention as applied to laying hens and the reduction of harmful cholesterol and the increase in beneficial cholesterol in poultry eggs.

FIG. 1 and Table 1 show the hematocrit response by the participants to waterleaf supplements. All Figures and Tables show an average component level of each of the 21 participants' measured levels. The asterisk (*) in each Figure and Table indicates that the means differed ($P<0.05$) from Week 1 (pretreatment). The probability of error was less than 5% ($P<0.05$). The pretreatment level (Week 1) shown in each Figure and Table represents the average measured level prior to any treatment or ingestion of waterleaf supplement. No statistically significant difference existed in average hematocrit level between the pretreatment level of Week 1 and the level of Week 2. However, a gradual increase in hematocrit level each week to Week 5 was observed, showing a net statistically significant difference between the Week 1 and Week 5 level of an increase of 8.1%. The Week 5 hematocrit level was significantly higher than the level at Week 1. The average level at Week 4 decreased slightly from Week 3 likely due to Thanksgiving holiday meals and to additional volume or consumption of foods not contained in American Heart Association Diet 1.

Figure 2:
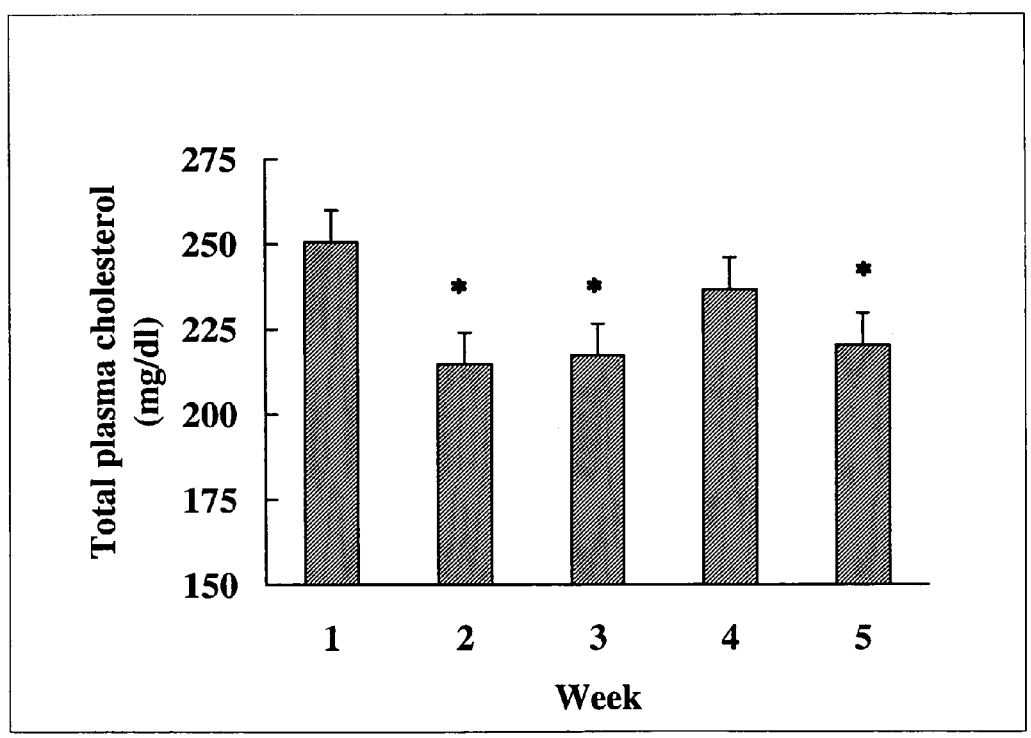
FIG. 2 is a graphical illustration of the changes in total plasma cholesterol levels in milligrams per deciliter (mg/dl) in hypercholesterolemic human adults fed 6 g/d of freeze-dried leaf supplements of waterleaf for 5 weeks. Total plasma total cholesterol levels were significantly reduced at Weeks 2, 3, and 5.
Figure 3:
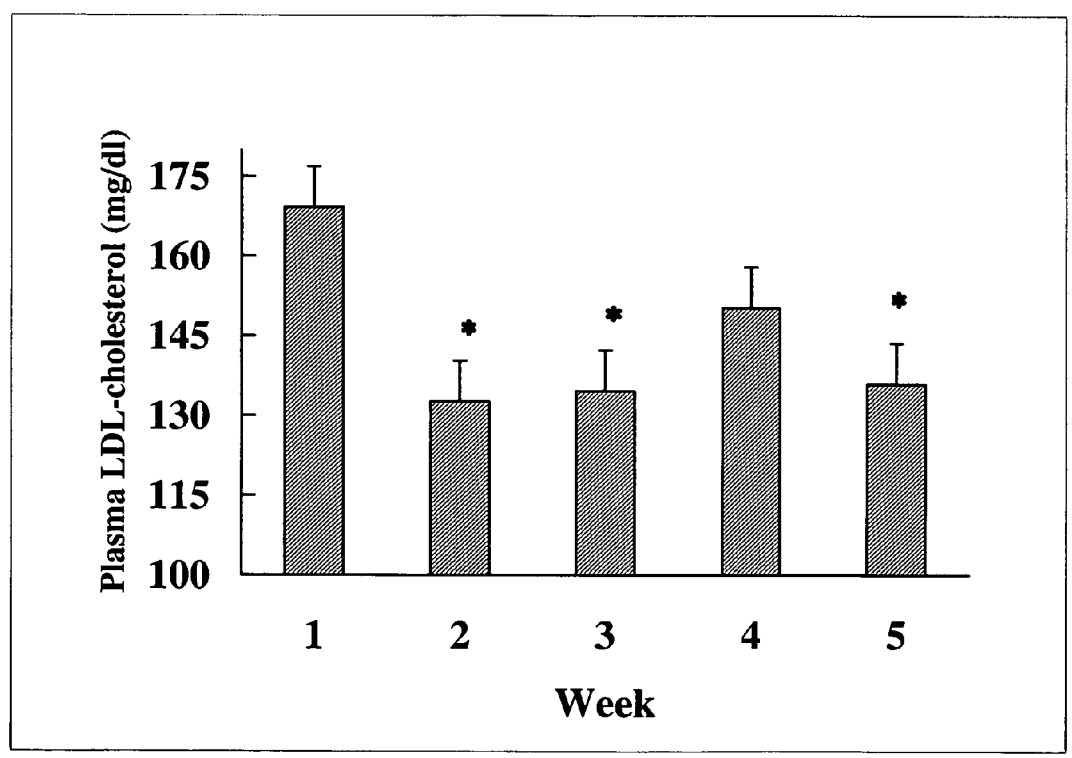
FIG. 3 is a graphical illustration of the changes in plasma LDL-cholesterol levels (mg/dl) in hypercholesterolemic human adults fed 6 g/d of freeze-dried leaf supplements of waterleaf for 5 weeks. LDL-cholesterol levels were significantly reduced at Weeks 2, 3, and 5.
Figure 4:
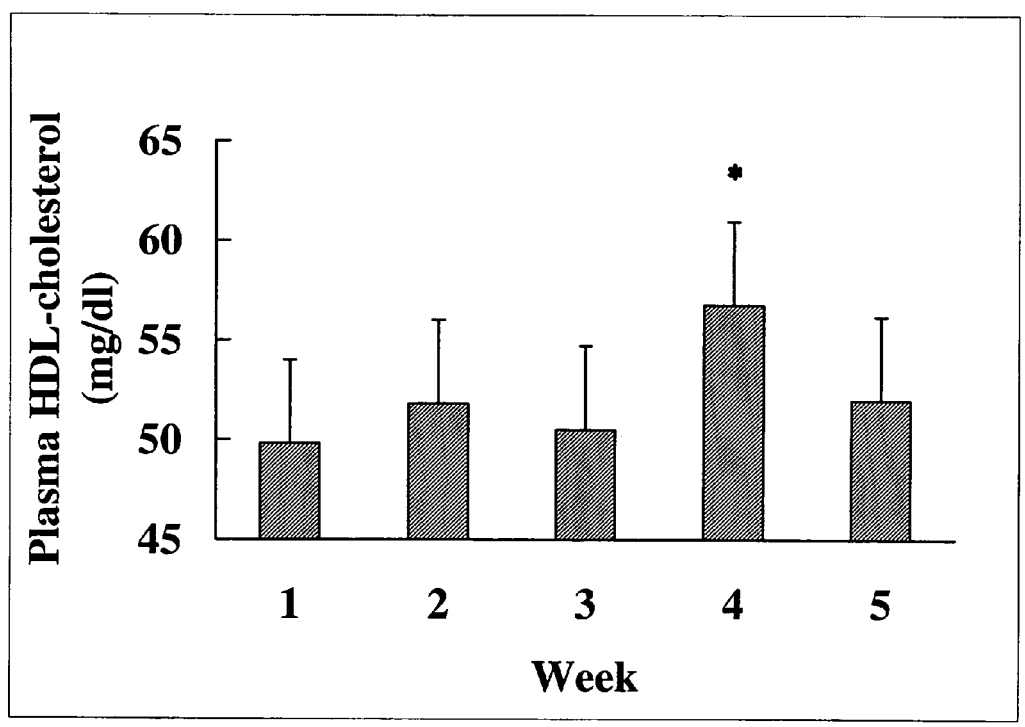
FIG. 4 is a graphical illustration of the changes in plasma HDL-cholesterol levels (mg/dl) in hypercholesterolemic human adults fed 6 g/d of freeze-dried leaf supplements of waterleaf for 5 weeks. Significant differences in plasma HDL-cholesterol levels were observed between Week 1 and Week 4.
Figure 5:
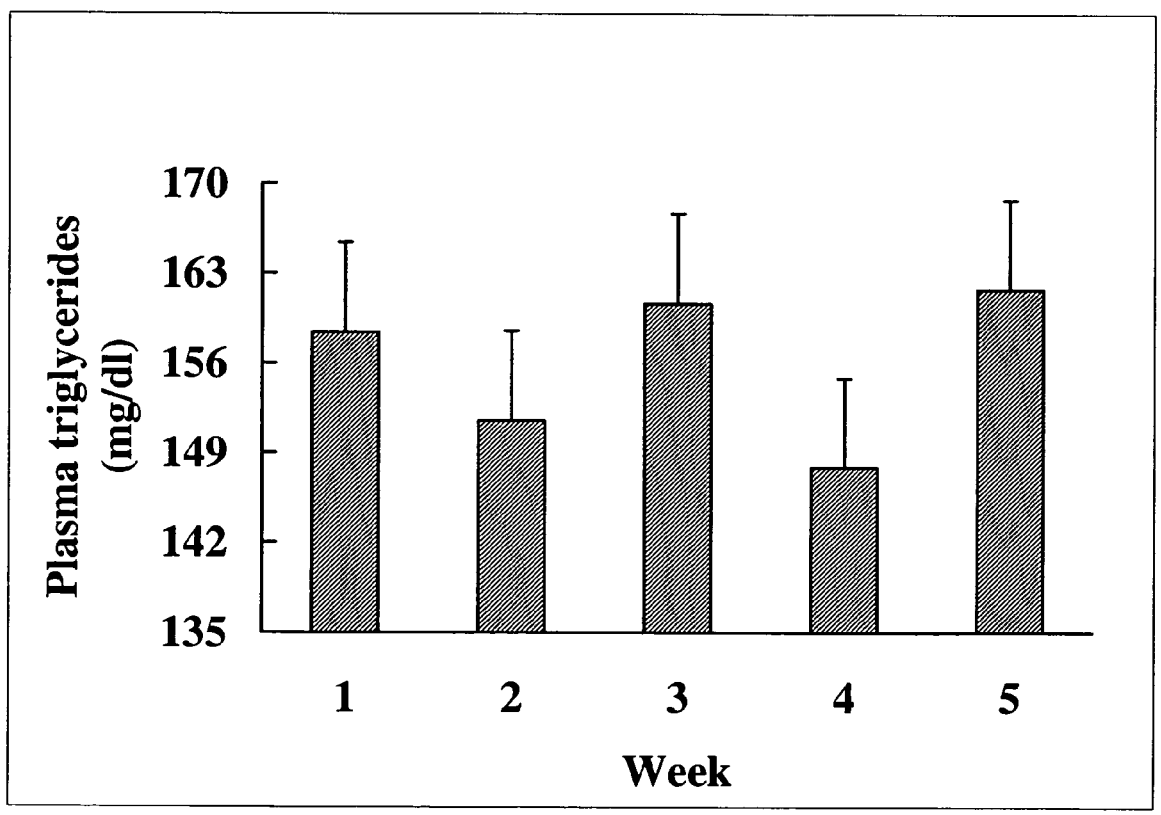
FIG. 5 is a graphical illustration of the changes in plasma triglyceride levels (mg/dl) in hypercholesterolemic human adults fed 6 g/d of freeze-dried leaf supplements of waterleaf for 5 weeks. No statistically significant differences were evident between the pretreatment (Week 1) plasma triglyceride levels and the plasma triglyceride levels measured in the remaining sampling periods. Variations existed among the measurement periods, but no significant differences were observed.

Dietary supplementation of freeze-dried waterleaf supplements (6 grams/day) for 5 weeks reduced total plasma cholesterol and LDL-cholesterol in free-living hypercholesterolemic human participants. Differences in total plasma cholesterol were significant between the level of Week 1 and those levels of Weeks 2, 3, and 5. Total plasma cholesterol was reduced by waterleaf supplements from 250.66 mg/dl at Week 1 to 214.71 mg/dl at Week 2, and by 12% at Week 5 (FIG. 2 and Table 2). Similarly, LDL-cholesterol was significantly reduced by waterleaf supplements at Weeks 2, 3, and 5. The Week 1 average level of 169.19 mg/dl was reduced to 135.9 mg/dl at Week 5, a reduction of 19.9% (FIG. 3 and Table 3). An increase in HDL-cholesterol was observed in the participants from the pretreatment Week 1 level of 49.8 mg/dl to 56.76 mg/dl at Week 4 (FIG. 4 and Table 4). Plasma triglycerides were not influenced by waterleaf likely due to the normal triglyceride levels maintained by the participants. No statistically significant differences were observed or evident between the pretreatment (Week 1) plasma triglyceride levels and those levels measured in the remaining sampling periods of Weeks 2 through 5. Variations existed among the measurement periods, but no significant differences were observed. The range of plasma triglycerides in the experimental participants was normal and ranged from 137.0 mg/dl to 154.2 mg/dl throughout the entire experimental period, indicating that the waterleaf supplement did not interfere with normal physiological levels (FIG. 5 and Table 5). It is noteworthy to observe that waterleaf supplements did not interfere with normal levels of plasma triglycerides.

Table 6 shows that the chemical composition on a dry matter (DM) basis of waterleaf showed high levels each of crude protein (21.9%), total lipids (4.2%), ash (19.6%), and pectin (19.5%). It also shows that waterleaf contains exceptionally high levels of vitamin C and vitamin E. The present invention and methods of harvesting and processing of waterleaf, and the level of consumption thereof, contributed significantly to the preservation of the nutrient content and consequently to its biological activity and the resultant positive effects on the health of the human participants.

The uniqueness of waterleaf and its nutritional composition lies in its ability to reduce total plasma cholesterol and LDL-cholesterol and in its high potential to increase HDL-cholesterol and blood hematocrit levels. The present invention may also prove to effectively reduce levels of other heretofore unidentified or known unhealthy compounds and increase levels of other heretofore unidentified or known healthy compounds. Waterleaf supplement also contains high levels of soluble fiber (pectin) and antioxidants, which have been shown to reduce the risk of heart disease. Though waterleaf naturally contains all the essential nutrients needed for optimum cardiovascular health, the present invention demonstrates for the first time how the nutritional qualities of waterleaf can be maximized to reduce the incidence of cardiovascular diseases in humans. The waterleaf leaf powder supplements used in the experiment may take various forms including, but not limited to, powder, tablet, pill, gel, capsule, liquid, or suspension. These supplements may also take the form of a dietary supplement and a dietary supplement in the form of a bar. Additionally, extract of waterleaf leaves comprising compounds such as protein, minerals, fiber, ash, lipids, pectin, vitamin C, vitamin E, Beta-carotene, and anti-oxidants can be obtained from the leaves and used for such nutritional purposes by the food industry as dietary supplements. Based on the experiment results, the present invention restores n-3 fatty acids to the diet and balances n-6 fatty acids to n-3 fatty acids in the diet.

Since about fifty species of waterleaf plants are known to exist in the tropics, subtropics, and warmer parts of the world, the potential for waterleaf to become a new agricultural crop in the United States is promising. The applicability of waterleaf as a dietary supplement for reducing harmful cholesterols and increasing beneficial cholesterols, and thereby preventing or treating coronary heart disease, is potentially far-reaching. Such applicability includes human diets as well as diets for all monogastric animals, including poultry and swine, as well as grazing animals. Furthermore, the ability of waterleaf to adapt to soil and weather conditions in Mississippi and the southern United States, and its resistance to insect pests, provides opportunities for farmers to commercialize the crop for both income generation and health benefits.

The present invention and its methods find primary applicability in the production of nutritional supplements containing increased Omega 3-fatty acids, antioxidants, and pectin for health-conscious consumers who wish to benefit from the neutracetical properties of waterleaf. The present invention has applicability as nutritional supplements for all humans who have or are susceptible to high blood cholesterol. The present invention also has applicability as feed or nutritional supplements for the improvement of poultry egg quality and the product quality of meat animals and of meat quality.

The above is a detailed description of embodiments of the present invention. All embodiments disclosed and claimed herein can be easily executed in light of this disclosure. Those of ordinary skill in the art, in light of the present disclosure, should recognize and understand that a wide variety of obvious alternatives, variations, and modifications of the embodiments disclosed herein can be selected and made without departing from the true scope and spirit of the present invention. The invention is described both generically and regarding specific embodiments, while the full scope of the invention is set out in the claims and their equivalents that follow. The specific tests and treatment results presented further explain the invention and are not to be interpreted or inferred as limiting thereof. The claims and specification should not be construed to unduly narrow the complete scope of protection to which the present invention is entitled. The disclosure and appended claims are intended to cover all modifications that may fall within the scope of the claims.

TABLE 1

Hematocrit Levels (%)

| Week | Hematocrit Levels (%) |
|---|---|
| 1 | 40.73 |
| 2 | 41.31 |
| 3 | 43.4 |
| 4 | 42.6 |
| 5 | 44.46* |

Note:
Table 1 corresponds to FIG. 1.
*indicates the means differ ($P < 0.05$) from Week 1.

TABLE 2

Total Plasma Cholesterol Levels (mg/dl)

| Week | Total Plasma Cholesterol (mg/dl) |
|---|---|
| 1 | 250.66 |
| 2 | 214.71* |
| 3 | 217.21* |
| 4 | 236.61 |
| 5 | 220.3* |

Note:
Table 2 corresponds to FIG. 2.
*indicates the means differ ($P < 0.05$) from Week 1.

TABLE 3

Plasma LDL-Cholesterol Levels (mg/dl)

| Week | Plasma LDL-Cholesterol (mg/dl) |
|---|---|
| 1 | 169.19 |
| 2 | 132.59* |
| 3 | 134.58* |
| 4 | 150.29 |
| 5 | 135.9* |

Note:
Table 3 corresponds to FIG. 3.
*indicates the means differ ($P < 0.05$) from Week 1.

TABLE 4

Plasma HDL-Cholesterol Levels (mg/dl)

| Week | Plasma HDL-Cholesterol (mg/dl) |
|---|---|
| 1 | 49.8 |
| 2 | 51.82 |
| 3 | 50.5 |
| 4 | 56.76* |
| 5 | 51.97 |

Note:
Table 4 corresponds to FIG. 4.
*indicates the means differ ($P < 0.05$) from Week 1.

TABLE 5

Plasma Triglyceride Levels (mg/dl)

| Week | Plasma Triglycerides (mg/dl) |
|---|---|
| 1 | 158.41 |
| 2 | 151.52 |
| 3 | 160.61 |
| 4 | 147.83 |
| 5 | 161.72 |

Note:
Table 5 corresponds to FIG. 5.

TABLE 6

Chemical Composition (DM) of Waterleaf Leaf Supplements

| ITEM | MEANS ± SEM$^\alpha$ |
|---|---|
| Crude Protein, % | 21.9 ± 0.14 |
| Crude Fiber, % | 1.5 ± 0.15 |
| Ash, % | 19.6 ± 0.01 |
| Total Lipids, % | 4.2 ± 0.17 |
| Pectin, % | 19.5 ± 0.41 |
| Vitamin C, ppm | 858.0 ± 0.35 |
| Vitamin E, mg/100 g | 29.0 ± 0.19 |
| Beta-Carotene, IU/kg | 64,048.3 ± 409.4 |

Note:
$^\alpha$Means ± SEM for six (6) samples.

We claim:

1. A method of reducing total plasma cholesterol and LDL-cholesterol and of increasing blood hematocrit and HDL-cholesterol in an animal in need thereof comprising feeding the animal an effective amount of food composition comprising at least about 3 grams of waterleaf leaves for a suitable period of time, wherein said leaves are obtained from waterleaf plants in full bloom.

2. The method as claimed in claim 1, wherein an effective amount of said food composition comprises at least about 3 grams of waterleaf leaves fed to said animal at least once per day.

3. The method as claimed in claim 2, wherein an effective amount of said food composition comprises at least about 3 grams of waterleaf leaves fed to said animal at lunch and at least about 3 grams of waterleaf leaves fed to said animal at dinner.

4. The method as claimed in claim 1, wherein said animal is a monogastric animal.

5. The method as claimed in claim 4, wherein said animal is a human.

6. The method as claimed in claim 5, wherein said human is a hypercholesterolemic human.

7. The method as claimed in claim 1, wherein said animal is a grazing animal.

8. The method as claimed in claim 4, wherein said monogastric animal is poultry.

9. The method as claimed in claim 4, wherein said monogastric animal is swine.

10. The method as claimed in claim 1, wherein said food composition is in the form of a powder, tablet, pill, gel, capsule, liquid, or suspension.

11. The method as claimed in claim 1, wherein said food composition is in the form of a dietary supplement.

12. The method as claimed in claim 11, wherein said dietary supplement is in the form of a bar.

13. A method of reducing total plasma cholesterol and LDL-cholesterol and of increasing blood hematocrit and HDL-cholesterol in an animal in need thereof comprising feeding the animal an effective amount of an extract of waterleaf leaves for a suitable period of time, wherein said leaves are obtained from waterleaf plants in full bloom.

14. The method as claimed in claim 13, wherein the waterleaf leaves extract comprises at least one compound selected from the group consisting of protein, minerals, fiber, ash, lipids, pectin, vitamin C, vitamin E, Beta-carotene, and anti-oxidants.

15. The method as claimed in claim 1, wherein said food composition is fed to said animal for at least five weeks.

* * * * *